(12) United States Patent
Artsyukhovich et al.

(10) Patent No.: US 7,292,323 B2
(45) Date of Patent: Nov. 6, 2007

(54) OPTICAL FIBER DETECTION METHOD AND SYSTEM

(75) Inventors: Alexander N. Artsyukhovich, Dana Point, CA (US); Bruno X. Lassalas, Irvine, CA (US); T. Scott Rowe, Dana Point, CA (US); Peter Nguyen, Garden Grove, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/273,123

(22) Filed: Nov. 14, 2005

(65) Prior Publication Data

US 2006/0103835 A1 May 18, 2006

Related U.S. Application Data

(60) Provisional application No. 60/627,758, filed on Nov. 12, 2004.

(51) Int. Cl.
*G01N 21/00* (2006.01)
(52) U.S. Cl. .................................................. 356/73.1
(58) Field of Classification Search .................. None
See application file for complete search history.

(56) References Cited

U.S. PATENT DOCUMENTS

| 4,215,937 A | 8/1980 | Borsuk |
| 4,381,882 A | 5/1983 | Sabine |
| 4,870,952 A | 10/1989 | Martinez |
| 5,085,492 A | 2/1992 | Kelsoe et al. |
| 5,780,846 A | 7/1998 | Angilella et al. |
| 5,993,072 A | 11/1999 | de Juan Jr. et al. |
| 5,993,442 A * | 11/1999 | Omori .................... 606/10 |
| 2003/0002822 A1 | 1/2003 | Ishihara et al. |
| 2006/0139633 A1* | 6/2006 | Puppels et al. ......... 356/301 |

* cited by examiner

*Primary Examiner*—Tu T. Nguyen
(74) *Attorney, Agent, or Firm*—Armando Pastrana, Jr.

(57) ABSTRACT

An optical fiber detector, and a method and system for optical fiber detection are disclosed. One embodiment comprises a receptacle, to receive and position an optical fiber connector, an infra-red ("IR") source for providing an incident IR beam onto a cross-sectional face of an optical fiber and a cross-sectional face of the optical fiber connector, and an IR detector for receiving a reflected IR beam from the face of the optical fiber and the face of the optical fiber connector and generating a detector signal representative of the intensity of the reflected IR beam, wherein the intensity of the reflected IR beam is representative of the presence and type of the optical fiber. It is contemplated that the optical fiber detector of this invention can be implemented or incorporated in any machine or system requiring connection of an optical fiber to a light source.

21 Claims, 2 Drawing Sheets

OPTICAL FIBER DETECTION METHOD AND SYSTEM

This application claims priority under 35 U.S.C. §119 to U.S. Provisional Patent Application No. 60/627,758 filed Nov. 12, 2004, the entire contents of which are incorporated herein by reference.

TECHNICAL FIELD OF THE INVENTION

The present invention relates generally to the field of fiber-optic connectors. In particular, the present invention relates to detection and identification of optical fibers inserted into a fiber-optic connector. Even more particularly, the present invention pertains to systems and methods for detecting and identifying optical fibers inserted into a fiber-optic connector in a fiber-optic illuminator.

BACKGROUND OF THE INVENTION

Typically, surgical procedures performed on a patient's eye require illuminating a portion of the eye so that a surgeon can properly observe the surgical site. Various different types of instruments are known and available for use by a surgeon to illuminate the interior of the eye. For example, a typical ophthalmic illuminator includes a handheld (probe) portion comprising a handle having a projecting tip and a length of optical fiber that enters a proximal end of the handle and passes through the handle and the tip to a distal end of the tip, from which light traveling along the optical fiber can project. The proximal end of the optical fiber can be positioned adjacent to a light source, such as in a high brightness illuminator, as known to those having skill in the art, to receive the light that is transmitted through the fiber. This type of handheld illuminator is typically used by inserting the probe tip through a small incision in the eye. In this way, light from the illumination light source is carried along the optical fiber, through the handpiece and emitted from the distal end of the probe to illuminate the surgical site for the surgeon. Ophthalmic illuminators that use a length of optical fiber to carry and direct light from a light source to a surgical site are well known in the art.

A common trait among surgical fiber-optic ophthalmic illuminators is that the handheld portion is connected to the light source by means of a fiber-optic connector, typically comprising an adaptor designed to be received in a socket operably adjacent to the light source in an enclosure housing the light source. However, connecting these prior art fiber-optic illuminators to the light source has involved some difficulties. Note that for purposes of the description contained herein, the terms "probe" and "fiber-optic illuminator" generally refer to the handheld portion of a typical ophthalmic illumination system, such a system typically comprising the handheld portion, to direct illumination from a light source housed in an enclosure, and the enclosure, which typically houses the light source and associated optics that guide light from the light source to the optical fiber of the probe, a power supply, electronics for signal processing, and associated connectors, displays and other interfaces, as known in the art.

Currently, fiber-optic illuminators and illumination sources are connected to one another via fiber-optic connectors that are typically difficult to operate, provide no indication of a proper connection between the optical fiber and the illumination source and cannot differentiate between different non-encoded optical fibers. For example, some currently existing illumination systems require an operator to manually deactivate a fiber-optic connection port when disconnecting the fiber-optic illuminator from the light source. These systems also typically do not provide a safeguard against either inadvertent operation of the light source without an illuminator connected or inadvertent disconnection of a fiber-optic illuminator from the light source when in operation. Either of these conditions can result in projecting an intense beam of light from the light source into, for example, an operating room, which can startle, distract or annoy the surgeon and staff during a surgery. Currently existing systems can thus easily cause potentially harmful disturbances during a surgical procedure.

Further, existing fiber-optic ophthalmic illuminator systems, although capable of detecting the presence of an optical fiber, cannot distinguish between different types of optical fibers unless the optical fiber connectors are specially encoded. In other words, prior art fiber-optic illuminator systems are capable of detecting the presence of a particular type of optical fiber connected to the illumination source enclosure, but they require encoding (e.g., an electrically encoded strip or a laser bar code) of the optical fiber connectors in order to do so. Other fiber-optic illumination systems can detect the presence of an optical fiber via micro switches, but provide no recognition capability.

Prior art optical illuminators are also typically connected to a light source via simple locking mechanisms, which can be unwieldy to operate and require a user to touch un-sterile parts of the ophthalmic illuminator system during a surgical procedure when doing so. For example, the Bausch & Lomb Millennium™ system comprises a swinging shutter at the fiber-optic connection port. The mechanical shutter has an axis of rotation above the connector. To connect an optical probe, the user must swing the shutter away to open the connector clearance hole and then insert the fiber connector of the fiber-optic illuminator. When the optical probe is removed, the shutter swings down by gravity and closes the connector hole. The disadvantage of such a shutter is that a user will normally need to use both hands to connect the optical probe and will touch the un-sterile swinging shutter.

Therefore, a need exists for an optical fiber detection method and system that provide for optical fiber detection, for optical fiber recognition without encoding of the fiber connector and for sterile connection of an optical illuminator to a light source.

BRIEF SUMMARY OF THE INVENTION

The embodiments of the optical fiber detection method and system of the present invention substantially meet these needs and others. One embodiment of the optical fiber detector of this invention comprises: a receptacle, to receive and position an optical fiber connector; an infra-red ("IR") source for providing an incident IR beam onto a cross-sectional face of an optical fiber and a cross-sectional face of the optical fiber connector; and an IR detector for receiving a reflected IR beam from the face of the optical fiber and the face of the optical fiber connector and generating a detector signal representative of the intensity of the reflected IR beam, wherein the intensity of the reflected IR beam is representative of the presence and type of the optical fiber. This embodiment of the optical fiber can further comprise an IR filter for filtering non-IR wavelengths from the reflected IR beam before the IR beam is received at the IR detector and signal processing and control means, for receiving and processing the detector signal to provide display, control or monitoring functions.

The signal processing and control means can comprise a printed circuit board, integrated circuitry, memory, and a processor. The receptacle can be part of an illuminator system enclosure housing a light source, wherein the receptacle is further operable to position the connector such that the optical fiber is optically coupled to the light source. The infra-red source can comprise an IR light emitting diode ("LED") and the IR detector can comprise a photodiode operable to detect IR wavelengths. The optical fiber can be embedded within the connector and operably coupled to the connector such that its cross-sectional face is exposed at a proximal end of the connector. The cross-sectional face of the optical fiber and the cross-sectional face of the optical fiber connector are preferably co-incident. The IR source can be positioned within a recessed threaded cavity operable to channel and direct the incident IR beam from the IR source and the IR detector can be positioned within a second recessed threaded cavity aligned to receive the reflected IR beam and channel and direct the reflected IR beam to the IR detector. The intensity of the reflected IR beam can vary, and is inversely proportional to the ratio of the area of cross-sectional face of the optical fiber reflecting the incident IR beam to the area of cross-sectional optical fiber connector reflecting the incident IR beam. This is to say that, typically, the intensity of the reflected IR beam will be inversely proportional to the diameter of the optical fiber cross-sectional face.

Other embodiments of the present invention can include a method for detecting an optical fiber and a system for detecting an optical fiber incorporating an optical fiber detector in accordance with the teachings of this invention. Embodiments of this invention can be implemented within any fiber-optic illuminator machine or system for use in ophthalmic or other surgery. Further, it is contemplated that the method and system for optical fiber detection of this invention can be implemented or incorporated in any machine or system requiring connection of an optical fiber to a light source. Other uses for an optical fiber detection method and system designed in accordance with the teachings of this invention will be apparent to those familiar with the art.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings, in which like reference numbers indicate like features and wherein.

DETAILED DESCRIPTION OF THE INVENTION

Preferred embodiments of the present invention are illustrated in the FIGUREs, like numerals being used to refer to like and corresponding parts of the various drawings.

The various embodiments of the present invention provide for the detection and recognition of an optical fiber inserted into an optical fiber connector port of an illumination source enclosure. The embodiments of this invention provide for optical fiber recognition without the need for special encoding of the fiber-optic connectors. Embodiments of the present invention direct radiation from an infrared ("IR") LED at an angle close to Brewster's angle onto the face of a connected optical fiber and its fiber connector. Light reflected from the face of the optical fiber and the optical fiber connector is detected at a photo-detector, which can be a photodiode. The photo-detector provides a signal representative of the intensity of the reflected light to processing means, which can be configured and operable to indicate the presence and type of optical fiber based on the photo-detector signal. In this way, a fiber-optic illuminator system implementing an embodiment of this invention can provide an indication to a user about the connection status of the fiber-optic illuminator, as well as an indication of the type of optical fiber connected to the illumination source.

The signal from the photo-detector of this invention can also be used to initiate control functions, such as locking out operation of the light source when there is no fiber-optic illuminator connected to the light source and/or automatically turning off the light source when a fiber-optic illuminator is disconnected from the light source. The embodiments of the present invention can thus eliminate the prior art problem of inadvertent light source operation without a connected fiber-optic probe. Further, the embodiments of this invention do not require encoded optical fiber connectors to differentiate between optical fiber types. The embodiments of this invention thus allow for a simple insertion and connection of a fiber-optic illuminator while maintaining sterile conditions, provide for non-contact optical fiber detection and allow for optical fiber recognition of existing optical fiber types, without encoding their connectors. The embodiments of this invention can take advantage of the optical properties of an optical fiber and its connector, such as core diameter, refractive index, and connector reflectivity, to recognize the optical fiber type.

Figure 1:
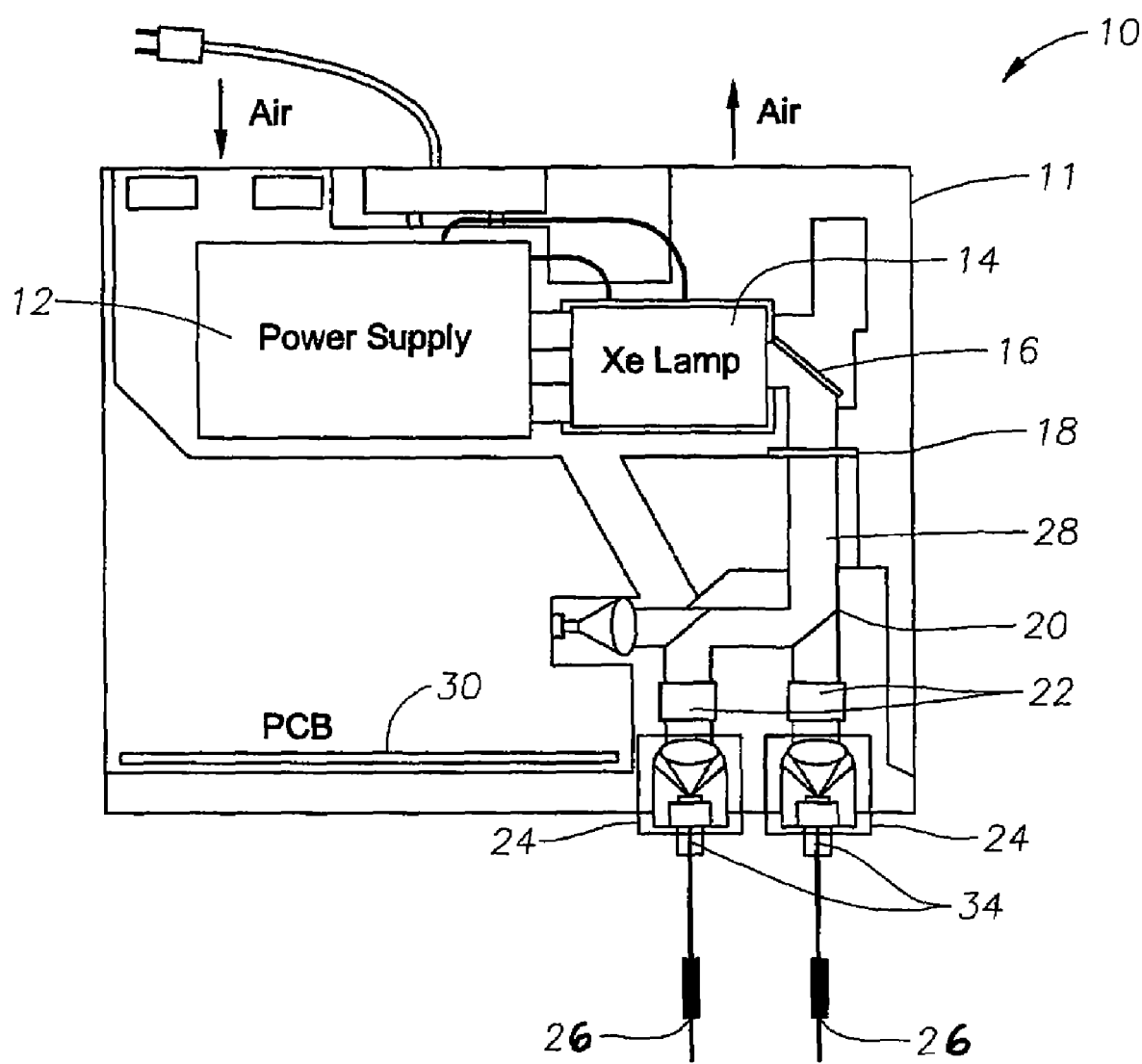
FIG. 1 is a simplified block diagram illustrating a high-brightness illuminator system implementing an embodiment of the present invention.

FIG. 1 is a simplified block diagram of a high brightness ophthalmic illuminator system incorporating an embodiment of the fiber-optic detection method and system of the present invention. Illuminator system 10 comprises power supply 12, an illumination source 14, cold mirror 16, a hot mirror 18, a beam splitter 20, mirror 21, attenuators 22, and an optical fiber detector 24. Illuminator system 10 also comprises an optical fiber probe 26, which comprises the handheld portion of illuminator system 10, including optical fiber 34, which is optically coupled to the illumination source 14 within enclosure 11. High brightness illuminator system 10 is exemplary only and is not intended to limit the scope of the present invention in any way. The embodiments of the present invention can be used in any such ophthalmic high brightness illuminator, medical laser, or in any system or machine requiring the connection of an optical fiber to a light source and in which optical fiber detection and/or recognition is desirable.

Optical source 14 of illuminator system 10 in this example comprises a xenon lamp, but it can comprise any suitable light source as known to those familiar with the art. Xenon lamp 14 emits light beam 28, which is directed along an optical path comprising cold mirror 16, hot mirror 18, beam splitter 20, attenuators 22 and optical fiber detectors 24. Cold mirror 16 and hot mirror 18 combine to remove the infrared components of light beam 28 (heat) and provide a cool visible light beam 28 to the downstream optical components, as will be known to those having skill in the art. Although high brightness illuminator system 10 is shown comprising two optical fiber detectors 24, it will be obvious to those skilled in the art that a single optical fiber detector 24 or multiple optical fiber detectors 24 can be implemented within a fiber-optic illuminator system. Illuminator system 10 further comprises a printed circuit board ("PCB") 30, or its electronic equivalent, to provide signal processing and control functions. PCB 30 can be implemented in any manner and configuration capable of performing the desired processing and control functions described herein, as will be apparent to those skilled in with the art. Optical fiber detectors 24 comprise a receptacle to receive an optical fiber probe 26, which is inserted into the receptacle (part of the enclosure) and optically coupled to illumination source 14 to direct light onto a desired site. This relationship is shown in greater detail in FIG. 2.

Figure 2:
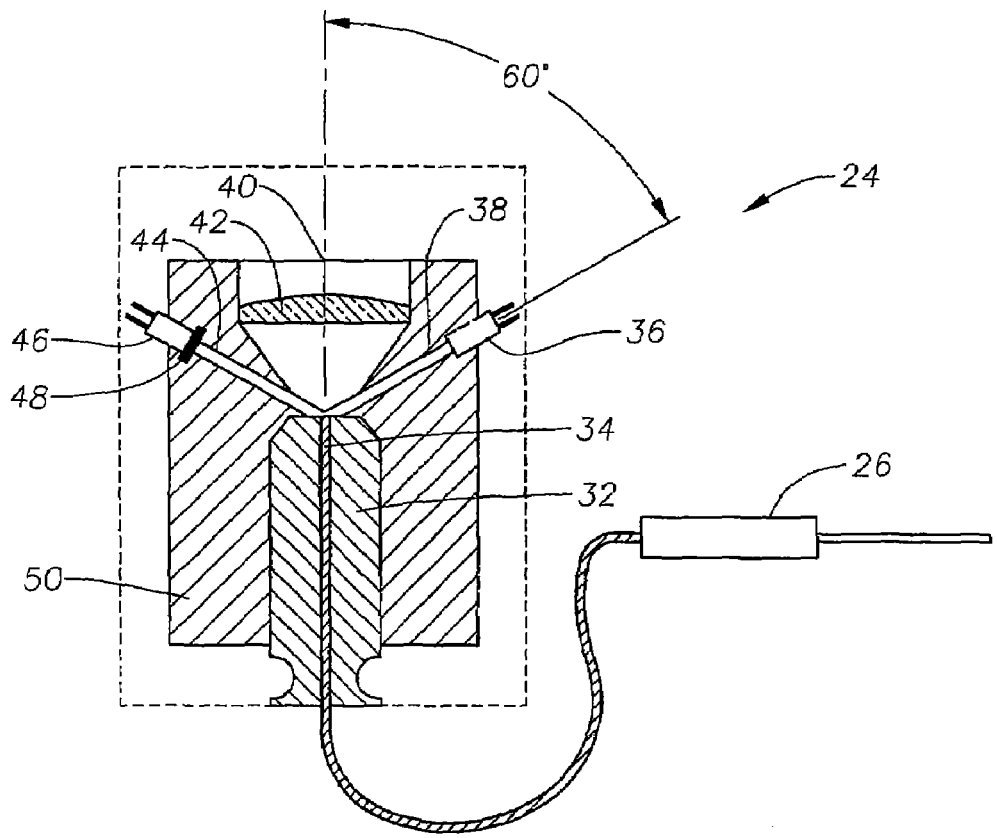
FIG. 2 is a simplified block diagram illustrating in greater detail an optical fiber detector according to this invention.

FIG. 2 is a simplified block diagram illustrating in more detail an optical fiber detector 24 of FIG. 1. Optical fiber detector 24 comprises a fiber receptacle 50 to receive fiber connector 32 of fiber probe 26. Fiber connector 32 houses within it an optical fiber 34. The proximal end of optical fiber 34 receives light transmitted from illuminating source 14, and optical fiber 34 transmits the received light to the handheld fiber probe 26. Optical fiber detector 24 further comprises an IR LED 36, IR filter 48 and photodiode 46. Not shown in FIG. 2 are the signal processing and control means of optical fiber detector 24, which can comprise, either as part of or in addition to PCB 30, a combination of integrated circuitry, memory, a processor, a power supply and a user interface, together operable to receive signals from photodetector 46 and other input sources, process the signals and provide desired display, control and/or monitoring functions. Any combination of components operable to provide these functions can be used with the embodiments of this invention, as will be apparent to those skilled in the art.

IR LED 36 can be a narrow angle IR LED whose output is channeled through a threaded hole (to suppress reflections) and directed onto an exposed proximal face of optical fiber 34, which can be co-incident to and enclosed by the proximal face of fiber connector 32. Incident IR beam 38 is directed from IR LED 36 to the optical fiber 34 face at an angle of incidence that is selected to be close (within 10°) to Brewster's angle (60°), to minimize reflection of the P-polarization component of the incident IR beam 38 from IR LED 36. The angle of incidence of IR beam 38 (and its corresponding angle of reflection to photodiode 46) is also selected to be close to Brewster's angle to suppress possible reflections from other glass or plastic components within optical fiber detector 24, and thus capture at photodiode 46 the reflected IR beam 44 (the reflected portion of incident IR beam 38) from the optical fiber 34 and fiber connector 32 faces, while minimizing other reflections. Other angles of incidence for IR beam 38 may exist that are capable of reflecting a desired portion of incident IR beam 38, in the form of reflected IR beam 44, to photodiode 46 such that photodiode 46 is operable to provide a signal representative of the optical fiber 34, and these angles are contemplated to be within the scope of the present invention.

Fiber-optic illuminators can have highly reflective fiber connectors (e.g., fiber connector 32, which surrounds the optical fiber 34). The highly reflective fiber connector 32 face will reflect a much greater amount of an incident beam, such as IR beam 38, than will the cross-sectional face of optical fiber 34. Thus, the amount of light reflected from the combined face of optical fiber 34 and fiber connector 32 is inversely proportional to the optical fiber 34 diameter. In other words, the larger the optical fiber 34 diameter is, the greater the amount of low-level S-polarized IR radiation from incident IR beam 38 will be reflected off the optical fiber 34/fiber connector 32 face, and the less the intensity of light that is received at photo-detector 46. Conversely, the smaller the diameter of optical fiber 32, the greater the amount of incident IR beam 38 that is reflected off the optical fiber 34/fiber connector 32 combined face, regardless of polarization. This is because the highly reflective (typically aluminum) fiber connector 32 face will be receiving and reflecting proportionally more of the incident IR beam 38.

Figures 3A, 3B, 3C:
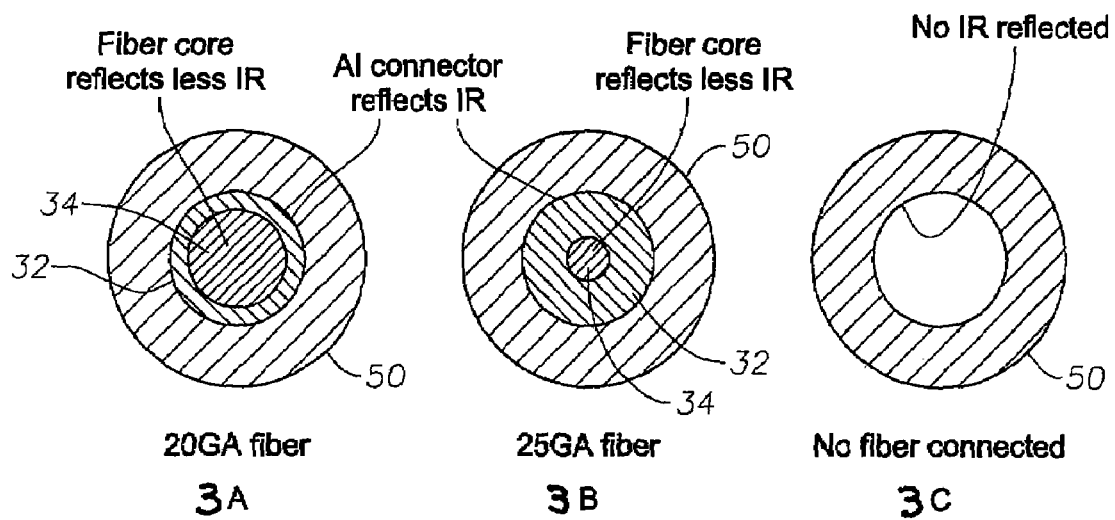
FIGS. 3A, 3B and 3C are diagrams illustrating the relationship between the ratio of incident IR beam diameter to optical fiber diameter and the amount of reflected IR, which the embodiments of the present invention take advantage of to differentiate between types of optical fibers.

FIGS. 3A, 3B and 3C illustrate the relationship between the amount of incident IR beam 38 reflected to the optical fiber 34 diameter. FIG. 3A shows a 20 gauge optical fiber 34 receiving an incident IR beam 38 having a diameter comparable to the optical fiber 34 diameter. In this case, the optical fiber 34 face will receive more, and reflect less of the incident IR beam 38 than would a comparably-sized area of the fiber connector 32. The face portion of fiber connector 32 receiving and reflecting incident IR beam 38 is relatively small in FIG. 3A, resulting in a less intense reflected IR beam 44 than would result with a smaller diameter optical fiber 34. FIG. 3B illustrates the case of a smaller diameter optical fiber 34, in this case a 25-gauge fiber. In FIG. 3B, the optical fiber 34 diameter is substantially smaller than the incident IR beam 38 diameter, resulting in most of the incident IR beam 38 being reflected off the much greater area aluminum face of the fiber connector 32. The resulting reflected IR beam 44 is more intense than for a larger diameter optical fiber 34, resulting in photodiode 46 receiving a more intense reflected IR beam 44 and generating a signal representative of a smaller optical fiber 34. Lastly, FIG. 3C illustrates the case where a fiber probe 26 is not connected to the high brightness illuminator enclosure (fiber receptacle 50), resulting in no reflection of incident IR beam 38. The resulting low (or null) signal from photodiode 46 represents that an optical fiber 34 has not been detected and hence no fiber probe 26 is connected.

The embodiments of the optical fiber detection system and method of this invention thus can employ an incident IR beam 38 from an IR LED 36 having a beam diameter slightly larger than the expected largest diameter optical fiber 34 that will be used, to detect and recognize different optical fibers. For example, a 1.6 mm IR beam diameter can effectively be used with an optical fiber having a diameter of 1.1 mm. Having an incident IR beam 38 diameter that is larger than the expected largest optical fiber 34 diameter ensures that when the largest diameter optical fiber 34 to be used with the ophthalmic illuminator system 10 is connected, the reflected IR beam 44 signal will be greater than zero (due to reflection from fiber connector 32). Therefore, removing the optical fiber 34 will result in an IR signal drop, which allows for optical fiber detection. When a smaller diameter optical fiber 34 is inserted into the detector, even more of incident IR beam 38 will be reflected, resulting in a still greater signal differential between the "fiber in" and the "fiber out" conditions. The amount of incident IR beam 38 that is reflected will depend on the optical fiber 34 diameter, the reflectivity of the surrounding fiber connector 32, the optical fiber 34 refractive index and the optical fiber mechanical registration in the connector (e.g., angle, decentration). By taking advantage of the difference in the intensity of reflected IR beam 44 for different optical fiber 34 diameters, the embodiments of this invention can be calibrated for an IR level read-out (signal) from the IR sensor (e.g., photodiode 46) representative of different optical fiber 34 diameters and can use this signal differentiation to recognize different optical fibers. In this way, the embodiments of this invention can easily distinguish, for example, between 20 gauge and 25 gauge optical fibers. Embodiments of this invention can further use different, for example, 20 gauge or 25 gauge, calibration data to control the intensity of the illumination source 14, depending on the optical fiber that is connected.

Photodiode 46 is used to detect the reflected IR beam 44 from the surface of the optical fiber 34 and fiber connector 32. Reflected IR beam 44 comprises the reflected component of incident IR beam 38, and, when received by photodiode 46, is operable to indicate both the presence of and the type of optical fiber 34 inserted into optical fiber detector 24. Any standard photodiode operable to detect the IR LED 36 beam in the form of reflected IR beam 44 can be used to implement the embodiments of this invention. Photodiode 46 can be located at the end of another threaded hole located symmetrically from IR LED 36 on an opposite side of optical fiber 34. Photodiode 46 is oriented at the same level of incidence (60° from the optical axis 40 of illumination beam 28, or from the normal to the optical fiber 34 cross-sectional face, in this case) as IR LED 36. IR filter 48 is oriented between photodiode 46 and reflected IR beam 44 to filter out other than infrared wavelengths from reaching photodiode 46. The embodiments of this invention can also be configured to modulate the IR LED 36 output to increase the signal-to-noise ratio of the reflected IR beam 44 received by photodiode 46 and thus the sensitivity of optical fiber detector 24. FIG. 2 schematically illustrates the basic layout and operation of an embodiment of the optical fiber detection method and system of the present invention.

The embodiments of the optical fiber detection method and system of this invention can be implemented such that they provide certain control functions of an illuminator system in which they are incorporated. For example, when the optical fiber detector 24 detects that an optical fiber has been removed (i.e., no optical fiber is present), it can provide a control signal to automatically shut off the illumination source 14. Similarly, optical fiber detector 24 can be configured to activate the optical fiber port (i.e., turn on the illumination source 14) only if a fiber is detected (inserted), and otherwise lock-out operation of the illumination source 14 such that it cannot be turned on without first inserting an optical fiber probe. This set-up can prevent the problem of prior art systems, in which the intense beam of light from the illumination source 14 is emitted from the empty optical fiber port of an illuminator system and distracts personnel in the operating room if the illumination source is inadvertently turned on without a probe inserted. In yet another embodiment, the optical fiber detector 24 of this invention can be configured to prevent operation of illumination system 10 if an optical fiber 34 is not fully inserted into the fiber receptacle 50. These functions can also be implemented in such a way that they can be manually overridden by direct action of an operator.

The embodiments of the optical fiber detector 24 of this invention, by detecting the amount of reflected light from the face of an optical fiber 34 and/or fiber connector 32, can detect the presence of an optical fiber 34 and can recognize the type of optical fiber 34 (e.g., a 20 gauge or a 25 gauge optical fiber). Further functionality is also provided in that optical fiber detector 24 allows manufacturers of an illuminator system implementing an embodiment of this invention to prevent the use of certain types of optical fibers that may not meet the requirements a manufacture wishes to maintain. For example, a manufacturer can block the use of competitive fiber-optic probes with its illuminator system. An illuminator system implementing an embodiment of the present invention can be configured to distinguish competitor probes and to permit operation only when a designated "acceptable" (recognized) type optical fiber (e.g., only from a particular manufacturer) is inserted. A recognized type optical fiber can be, for example, an optical fiber associated with a predetermined handheld probe type, the characteristics of which can be programmed in the signal processing and control means of an embodiment of the optical fiber detector of this invention.

Resolving between different optical fiber types, for example, between 20 gauge and 25 gauge optical fibers, allows an illuminator system 10 incorporating an embodiment of this invention to have different calibration schemes for different optical fibers. Currently existing illuminator systems typically calibrate power only for a 20 gauge optical fiber (or for only one gauge) and provide conversion coefficients for other gauge optical fibers. This presents a problem, however, in that a surgeon who, for example, is using a 25 gauge optical fiber with the illuminator system adjusted for maximum output, might then change to a 20 gauge optical fiber and, with the illuminator system set to maximum output, can burn the retina of a patient with what is now effectively a four times higher output. The embodiments of this invention can provide for switching between separate calibration curves for different type optical fibers (e.g., 20 gauge and 25 gauge). Based on the detection and recognition of the optical fiber type, a control signal can be generated by an optical fiber detector of this invention to set the high-brightness illuminator system to deliver approximately the same amount of illumination for each gauge optical fiber, by switching to the appropriate calibration curve when the optical fiber is changed.

The present invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims.

What is claimed is:

1. An optical fiber detector, comprising
    a receptacle, to receive and position an optical fiber connector;
    an infra-red ("IR") source for providing an incident IR beam onto a cross-sectional face of an optical fiber and a cross-sectional face of the optical fiber connector; and
    an IR detector for receiving a reflected IR beam from the face of the optical fiber and the face of the optical fiber connector and generating a detector signal representative of the intensity of the reflected IR beam, wherein the intensity of the reflected IR beam is representative of the presence and type of the optical fiber.

2. The optical fiber detector of claim 1, further comprising an IR filter for filtering non-IR wavelengths from the reflected IR beam before the IR beam is received at the IR detector.

3. The optical fiber detector of claim 1, further comprising signal processing and control means, for receiving and processing the detector signal to provide display, control or monitoring functions.

4. The optical fiber detector of claim 3, wherein the signal processing and control means comprise a printed circuit board, integrated circuitry, memory, and a processor.

5. The optical fiber detector of claim 1, wherein the receptacle is part of an illuminator system enclosure housing a light source and wherein the receptacle is further operable to position the connector such that the optical fiber is optically coupled to the light source.

6. The optical fiber detector of claim 1, wherein the infra-red source comprises an IR light emitting diode ("LED") and the IR detector comprises a photodiode operable to detect IR wavelengths.

7. The optical fiber detector of claim 6, wherein the IR LED is a narrow angle IR LED.

8. The optical fiber detector of claim 1, wherein the optical fiber is embedded within the connector and operably coupled to the connector such that the cross-sectional face is exposed at a proximal end of the connector.

9. The optical fiber detector of claim 8, wherein the cross-sectional face of the optical fiber and the cross-sectional face of the optical fiber connector are co-incident.

10. The optical fiber detector of claim 1, wherein the IR source is positioned within a recessed threaded cavity operable to channel and direct the incident IR beam from the IR source and wherein the IR detector is positioned within a second recessed threaded cavity aligned to receive the reflected IR beam and channel and direct the reflected IR beam to the IR detector.

11. The optical fiber detector of claim 1, wherein the incident IR beam is incident to the optical fiber cross-sectional face at an angle of incidence within 10 degrees of Brewster's angle, and wherein the IR detector is symmetrically positioned at the same level of incidence on an opposite side of the optical fiber cross-sectional face.

12. The optical fiber detector of claim 1, wherein the optical fiber connector cross-sectional face is more reflective than the optical fiber cross-sectional face.

13. The optical fiber detector of claim 1, wherein the optical fiber connector cross-sectional face material is aluminum.

14. The optical fiber detector of claim 1, wherein the incident IR beam has a cross-section diameter greater than a largest expected optical fiber cross-sectional face diameter.

15. The optical fiber detector of claim 1, wherein the intensity of the reflected IR beam is inversely proportional to the ratio of the area of cross-sectional face of the optical fiber reflecting the incident IR beam to the area of cross-sectional optical fiber connector reflecting the incident IR beam.

16. The optical fiber detector of claim 1, wherein the intensity of the reflected IR beam is inversely proportional to the diameter of the optical fiber cross-sectional face.

17. The optical fiber detector of claim 1, wherein the optical fiber is a 20 or 25 gauge optical fiber.

18. The optical fiber detector of claim 1, wherein the optical fiber is operably coupled to a handheld probe, and wherein the optical fiber detector is used to determine if the handheld probe is connected to an illumination system comprising the optical fiber detector and a light source.

19. The optical fiber detector of claim 18, wherein the optical fiber detector is operable to power-off the light source when a handheld probe is not connected to the illumination system.

20. The optical fiber detector of claim 18, wherein the optical fiber detector is operable to power-on the light source of the illumination system only when a recognized handheld probe is connected to the illumination system.

21. The optical fiber detector of claim 20, wherein the recognized handheld probe is a probe wherein the optical fiber is operable to reflect the incident IR beam such that the intensity of the incident IR beam is representative of a pre-determined handheld probe type.

* * * * *